United States Patent
Delaplane et al.

[11] Patent Number: 6,105,573
[45] Date of Patent: *Aug. 22, 2000

[54] HOOK AND PILE RETENTION SYSTEM FOR ANTI-DISCONNECT APPARATUS AND METHOD, FOR BREATHING SYSTEMS

[75] Inventors: David Delaplane; Robert Bohning, both of Simi Valley, Calif.

[73] Assignee: Hammer-Plane, Inc., Simi Valley, Calif.

[*] Notice: This patent is subject to a terminal disclaimer.

[21] Appl. No.: 09/080,185

[22] Filed: May 18, 1998

Related U.S. Application Data

[63] Continuation-in-part of application No. 09/010,883, Jan. 22, 1998, Pat. No. 5,975,080.

[51] Int. Cl.$^7$ ............................................. A61M 16/00
[52] U.S. Cl. ........................... 128/200.26; 128/207.14; 128/207.17; 128/207.29; 128/912; 128/DIG. 26
[58] Field of Search ..................... 128/200.26, 207.14, 128/207.15, 207.17, 207.29, DIG. 26, 912

[56] References Cited

U.S. PATENT DOCUMENTS

| | | | |
|---|---|---|---|
| 1,592,345 | 7/1926 | Drager | 128/207.17 |
| 1,835,757 | 12/1931 | Burchett | 128/207.17 |
| 2,765,792 | 10/1956 | Nichols | 128/207.17 |
| 2,928,387 | 3/1960 | Layne | 128/201.19 |
| 3,039,469 | 6/1962 | Fountain | 128/200.26 |
| 3,086,529 | 4/1963 | Munz et al. | 606/203 |
| 3,146,778 | 9/1964 | Krawiec | 128/DIG. 26 |
| 3,236,236 | 2/1966 | Hudson | 128/207.17 |
| 3,535,719 | 10/1970 | Murcott | 5/424 |
| 3,602,227 | 8/1971 | Andrew | 128/207.17 |
| 3,688,774 | 9/1972 | Akiyama | 128/200.26 |
| 3,774,616 | 11/1973 | White et al. | 128/DIG. 26 |
| 3,927,676 | 12/1975 | Schultz | 128/207.17 |
| 3,946,742 | 3/1976 | Eross | 128/207.17 |
| 3,973,569 | 8/1976 | Sheridan et al. | 128/207.15 |
| 3,987,798 | 10/1976 | McGinnis | 128/DIG. 26 |
| 4,018,221 | 4/1977 | Rennie | 128/207.18 |
| 4,027,666 | 6/1977 | Marx | 602/62 |
| 4,088,136 | 5/1978 | Hasslinger et al. | 604/179 |
| 4,235,229 | 11/1980 | Ranford et al. | 128/207.17 |
| 4,246,897 | 1/1981 | Muto | 128/207.15 |
| 4,256,099 | 3/1981 | Dryden | 128/200.26 |
| 4,304,228 | 12/1981 | Depel | 128/200.26 |
| 4,313,437 | 2/1982 | Martin | 128/207.17 |
| 4,331,144 | 5/1982 | Wapner | 128/207.17 |
| 4,485,822 | 12/1984 | O'Connor et al. | 128/207.17 |
| 4,527,559 | 7/1985 | Roxburg et al. | 128/207.17 |
| 4,548,200 | 10/1985 | Wapner | 128/207.17 |
| 4,598,705 | 7/1986 | Lichtenberger | 128/200.26 |
| 4,641,646 | 2/1987 | Schultz et al. | 128/207.14 |
| 4,738,662 | 4/1988 | Kalt et al. | 604/180 |
| 4,838,867 | 6/1989 | Kalt et al. | 604/180 |
| 4,844,061 | 7/1989 | Carroll | 128/DIG. 26 |
| 4,848,331 | 7/1989 | Northway-Meyer | 128/200.26 |
| 4,906,234 | 3/1990 | Voychehovski | 604/79 |
| 5,000,741 | 3/1991 | Kalt | 128/207.17 |
| 5,009,227 | 4/1991 | Nieuwstad | 128/207.17 |
| 5,010,884 | 4/1991 | Van Derdoes et al. | 128/207.17 |
| 5,042,477 | 8/1991 | Lewis | 128/207.17 |
| 5,054,482 | 10/1991 | Bales | 128/207.14 |
| 5,056,515 | 10/1991 | Abel | 128/207.15 |
| 5,069,206 | 12/1991 | Crosbie | 128/207.17 |
| 5,101,822 | 4/1992 | Kimmel | 128/207.14 |
| 5,123,410 | 6/1992 | Green et al. | 128/207.17 |
| 5,282,463 | 2/1994 | Hammersley | 128/207.15 |
| 5,357,952 | 10/1994 | Schuster et al. | 128/207.17 |
| 5,413,095 | 5/1995 | Weaver | 128/DIG. 26 |
| 5,471,980 | 12/1995 | Varner | 128/207.17 |
| 5,671,732 | 9/1997 | Bowen | 128/DIG. 26 |
| 5,782,236 | 7/1998 | Ess | 128/207.17 |

*Primary Examiner*—Aaron J. Lewis
*Attorney, Agent, or Firm*—William W. Haefliger

[57] ABSTRACT

A method of connecting flexible first band structure to a tracheostomy neck plate, the neck plate having a first wing projecting laterally, the method including providing first anchoring structure including a clip on the wing, the band structure connectible to the anchoring structure; and providing first adjustable hook and pile connections for retaining the band structure adjustably connected relative to the anchoring structure.

10 Claims, 7 Drawing Sheets

HOOK AND PILE RETENTION SYSTEM FOR ANTI-DISCONNECT APPARATUS AND METHOD, FOR BREATHING SYSTEMS

This application is a continuation-in-part of U.S. application Ser. No. 09/010,883 filed Jan. 22, 1998, now U.S. Pat. No. 5,975,080, incorporated herein by reference.

BACKGROUND OF THE INVENTION

This invention relates generally to use of tracheostomy tubes and associated equipment, and more particularly is addressed to the problem of inadvertent disconnection of elements of such equipment, which can lead to unwanted interruption of breathing.

This invention improves upon the highly advantageous apparatus and method disclosed in U.S. Pat. No. 5,282,463 to Hammersley, and incorporated herein by reference.

Tracheostomy plates have been commonly metallic or plastic. Clips were used on such plates to anchor the tracheostomy tie band (i.e., "ties"). Older type tracheostomy ties consisted of twill tape that was clumsily tied to each side of the tracheostomy plate, wrapped around the patient's neck, then tied together on the side of the patient's neck.

Later, with the advent of VELCRO™, tracheostomy ties became a little easier to use. Today, tracheostomy ties consist of a variety of materials, such as foam padding, elastic cloth, and wide and narrow materials, to enhance patient comfort. However, all of the tracheostomy ties mentioned above utilize the technique of feeding the tracheostomy tie through the eyelet provided on the tracheostomy tube plate, then fastening in some manner by either tying or using VELCRO™ material.

When the caregiver applies a tracheostomy tie in the conventional manner, the tracheostomy tie is applied under the plate. Some caregivers utilize hemostats or needle holders to attempt to pull the tracheostomy tie through the tie opening, occasionally pinching the patient's skin rather than grabbing the tie. Both of these methods can cause significant discomfort to the patient, while the tracheostomy tube is being manipulated.

The other negative is the time factor. Especially in the current health care market, time is of the essence. If time can be saved in the application of a tracheostomy tie, it would be welcomed.

SUMMARY OF THE INVENTION

This invention relates generally to the use of tracheostomy tubes and associated equipment; more particularly, it addresses the problem of securing a tracheostomy tube onto a patient's neck and additionally securing the ventilator breathing circuit onto the tracheostomy plate.

It is a major object of the invention to provide method and means for preventing inadvertent disconnection of breathing system tubing from associated tracheostomy tubes. Basically, use is made of a neck plate usually carried by the tracheostomy tube and a connector frictionally and telescopically connectible to the tube, as will be seen. In this environment, the basic combination of the invention includes retention apparatus for connecting flexible band means to a tracheostomy neck plate, the neck plate having a wing projecting laterally. One form of the retention apparatus comprises:

a) clip means configured to embrace the wing as the clip means is displaced relative to the wing, the band means attached to the clip means, b) and a detent connection element positioned on the clip to releasably connect to the wing in response to the relative displacing of the clip to embrace the wing.

Another object includes provision of the clip means to have guide means thereon to guide the relative displacement to releasably connect the clip to the wing at a predetermined connection locus, the wing tapering to interfit clip leg means when the detent connects to the wing. That locus is typically defined by shoulders on the clip means and wing that interengage in response to the lateral displacement of the clip means relative to the wing.

Yet another object is to provide a shoulder-defining tang projecting toward and into an opening defined by the wing. In this regard, the wing defined by the plate typically forms the opening extending in or through the wing, allowing easy push out removal of the tang upon resilient bending up of the wing, for releasing the clip from the wing and plate. The latter may consist of resiliently bendable plastic material.

A further object includes provision of a tracheostomy tube retention band means, and anchoring the retention band to the clip. A retention band grip may be provided at the clip for anchoring the retention band to the clip, instead of to the plate, for ease of application.

Dual such slots may be provided in respective association with the first wing, and also with a second wing defined by the plate, for anchoring the retention band to the clip at dual grip locations, there being a tracheostomy tube carried by the plate and located between the grips, and including auxiliary dual grips on the respective clip for anchoring neck band means. The auxiliary grip is angled relative to the tang on the clip to provide a lever for bending the clip to enable tang removal from the opening, for clip release.

Yet another object of the invention is to provide a method of connecting flexible first band means to a tracheostomy neck plate, the neck plate having a first wing projecting longitudinally, the method including:

a) providing first anchoring means, including a clip on the wing, the band means connectible to the anchoring means, b) and providing first adjustable hook and pile connections for retaining the band means adjustably connected to the first anchoring means.

Typically, the first anchoring means is configured to be anchored to a first opening through the neck plate, the clip has a section raised above the opening, the method includes the step of anchoring the clip to the opening, to pass the band means; and the band means includes a first ribbon fitting about the clip raised section.

An additional object includes providing the band means to include elongated padding, and locating one of the band hook and pile connections on the first ribbon, and the other of the hook and pile connections on the padding. The padding is typically provided to have width greater than the width of the ribbon, and the method may include widthwise adjustably interconnecting the ribbon and padding at the hook and pile connections to selectively position the padding widthwise of the neck plate.

Another object includes provision of a neck plate second wing, and includes providing second anchoring means, including a second clip on the second wing, the band means also connectible to the second clip, and the method includes providing second adjustable hook and pile connections for retaining the band means adjustably connected to the second anchoring means.

Yet another object includes providing the band means to include elongated padding having opposite end portions, and attaching first and second ribbons to the padding opposite end portions, and to project from those opposite end portions, the ribbons defined by the first and second anchoring means.

A yet additional object includes locating one of the hook and pile connections of the first anchoring means on the first ribbon, and the other of said hook and pile connections of the first anchoring means on the end portion of the elongated padding, and locating one of the hook and pile connections of the second anchoring means on the second ribbon, and the other of the hook and pile connections of the second anchoring means on the other end portion of the elongated padding.

In this regard, the padding end portions may advantageously have widths greater than the width of the ribbons, and the ribbons widthwise adjustably interconnected at the hook and pile connections to selectively position the padding widthwise, relative to the neck plate wings.

These and other objects and advantages of the invention, as well as the details of an illustrative embodiment, will be more fully understood from the following specification and drawings, in which:

DETAILED DESCRIPTION

Figure 6:
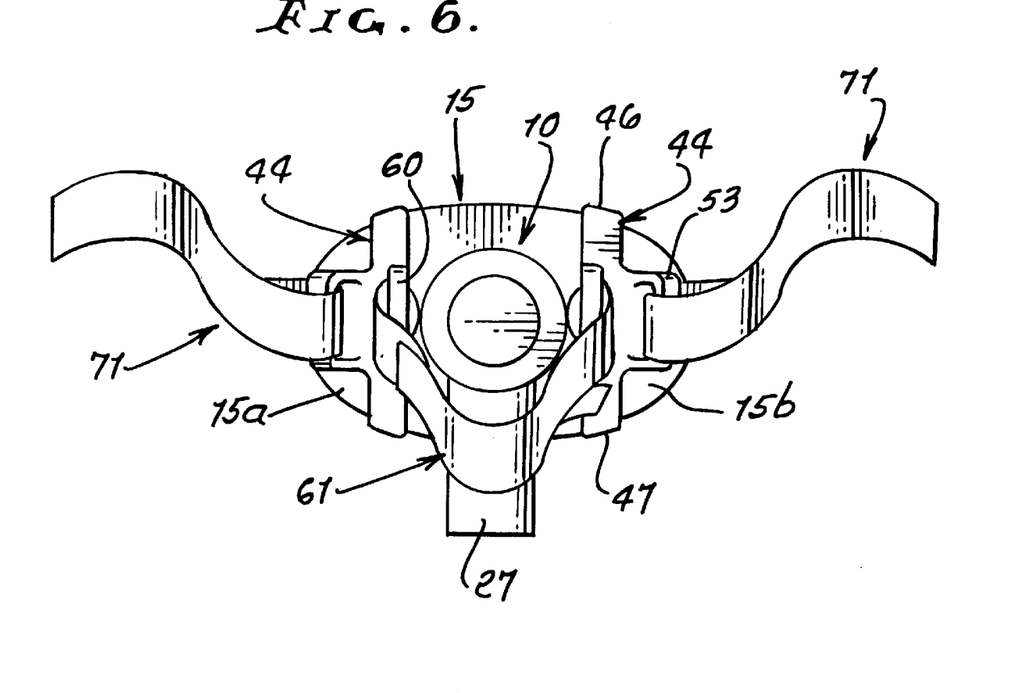
FIG. 6 is a view like FIG. 5, and also showing retention band means attached to the two clips.
Figure 8:
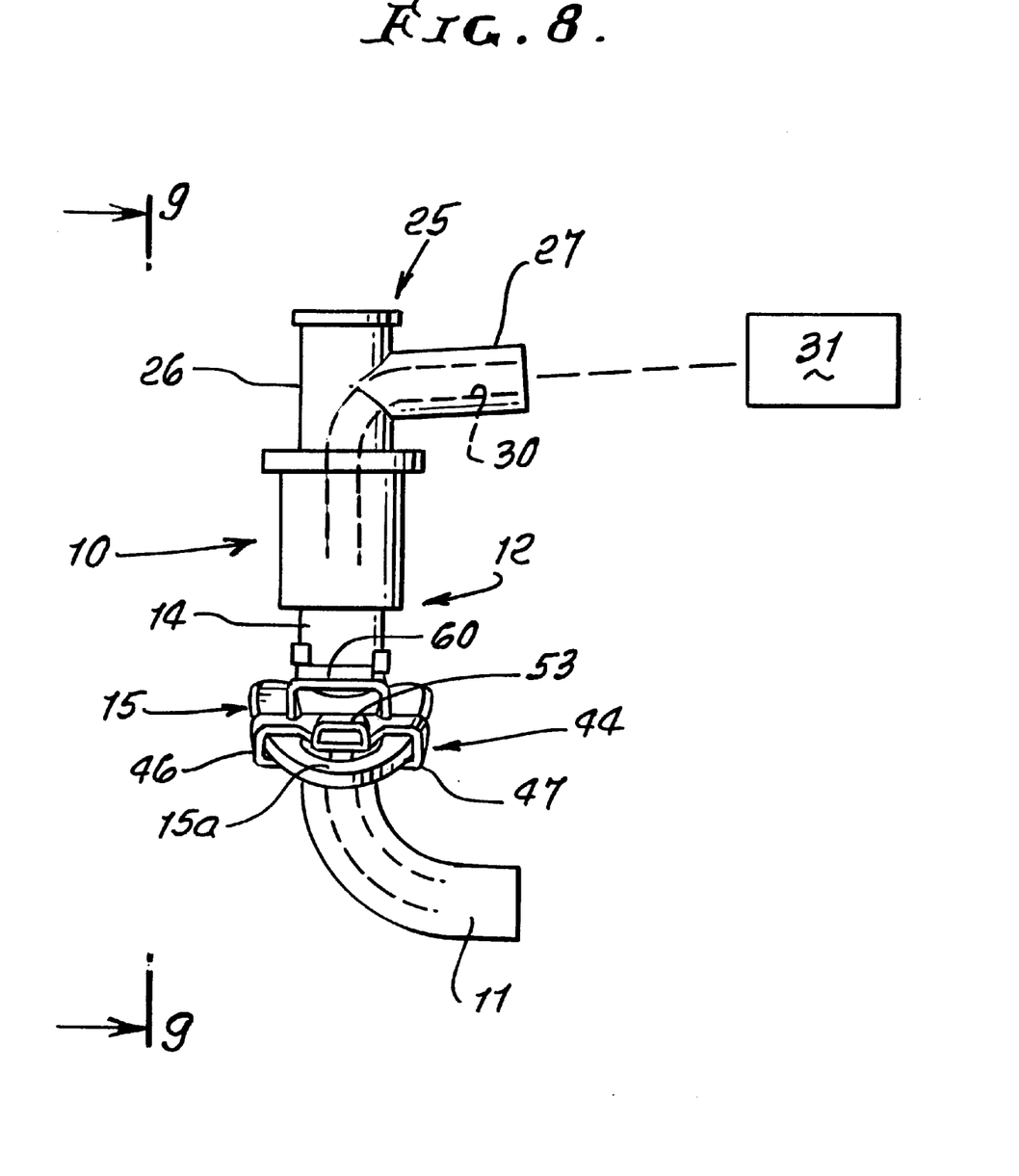
FIG. 8 is a side elevational view taken on lines 8—8 of FIG. 5.
Figure 9:
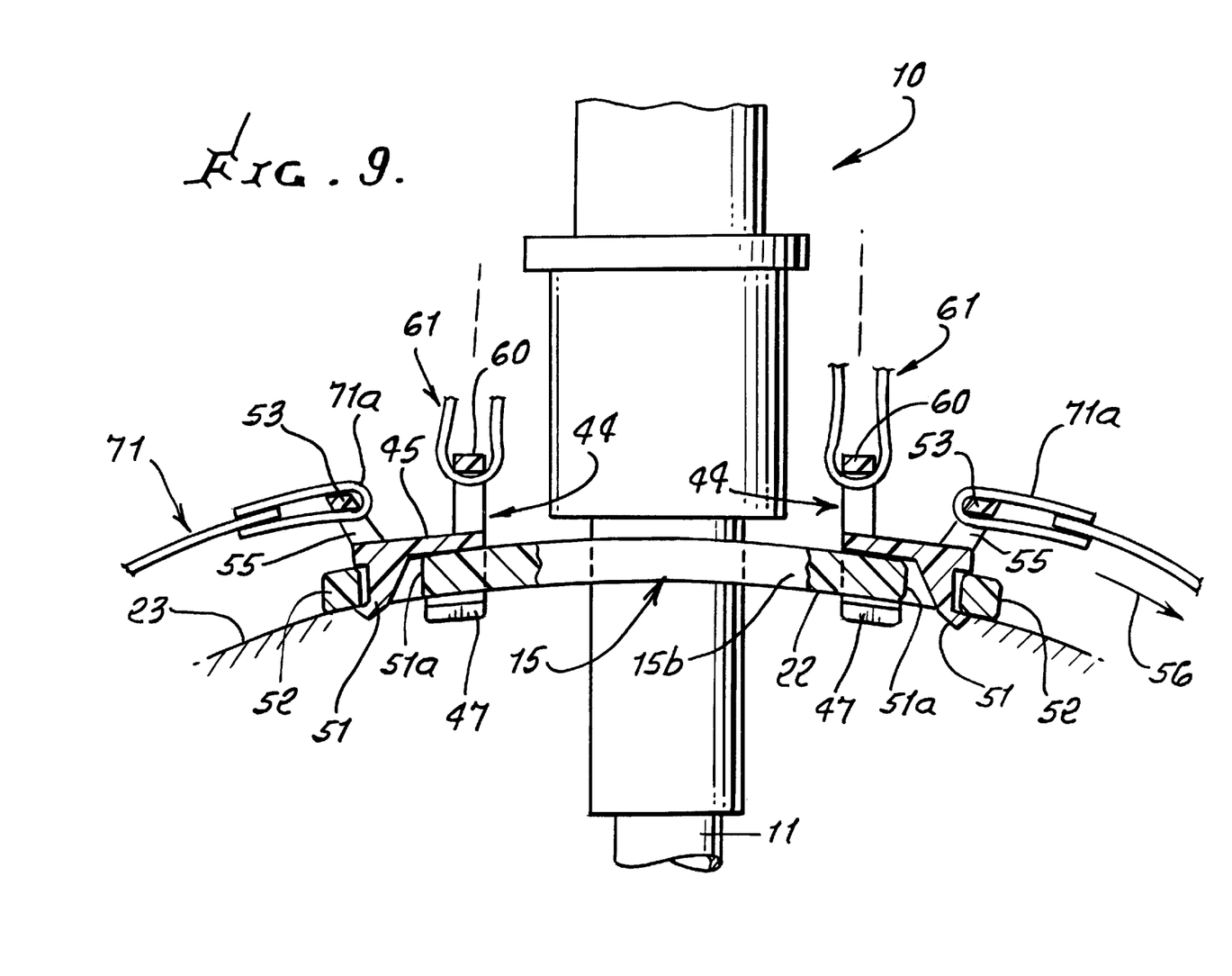
FIG. 9 is a front elevational view taken on lines 9—9 of FIG. 8.

In FIGS. 6, 8, and 9, a tracheostomy tube assembly 10 includes an elongated, curved, outer tube section 11 terminating at an enlarged, tubular head section 12. The assembly 10 also commonly includes an inner tube 14 communicating with section 12. A neck plate 15 is carried by section 12, to extend at opposite sides thereof. The plate has wings 15a and 15b which project oppositely, and which narrow in width, in opposite directions 16 and 17. The plate may be oval-shaped as shown.

Wing edges appear at 18–21. Edges 18 and 19 taper in direction 16; and edges 20 and 21 taper in 15 direction 17. The plate also has a face 22 with curvature to fit on a patient's neck 23, when tube section 11 is received through a neck opening and into the trachea. Various other forms of neck plates may be used. A duct, such as an elbow or bend 25, has legs 26 and 27. The elbow leg 27 has a bore 30 to pass air from a breathing system 31 to the tube 11.

In accordance with the invention, improved apparatus is provided to connect a flexible band means to the tracheostomy plate. The band means appears at 71 in FIG. 9 and has opposite end loops 71a. The apparatus comprises:

a) clip means configured to embrace the wing as the clip means is displaced relative to the wing, the band means attached to the clip means, b) and a detent connection element positioned on the clip to releasably connect to the wing in response to the relative displacing of the clip to embrace the wing.

Figure 1:
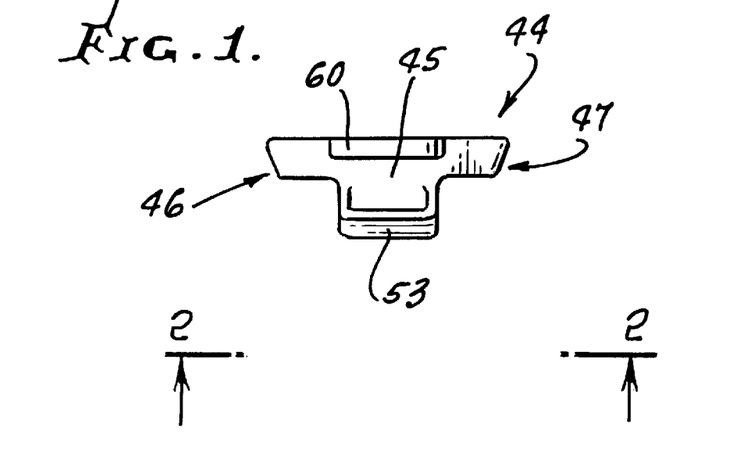
FIG. 1 is a top plan view of a clip.
Figure 2:
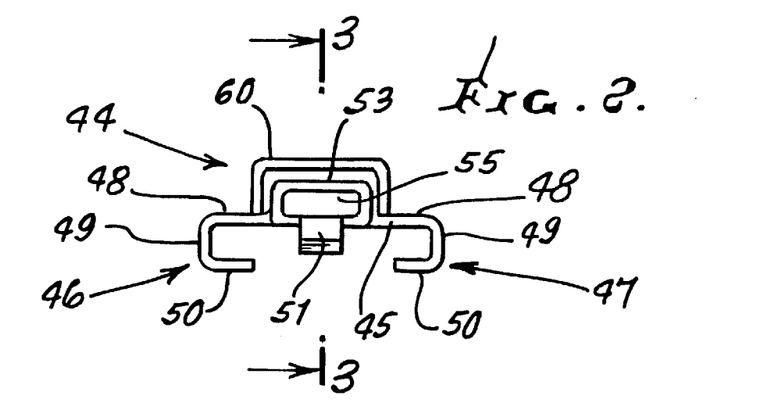
FIG. 2 is a front elevation view taken on lines 2—2 of FIG. 1.
Figure 3:
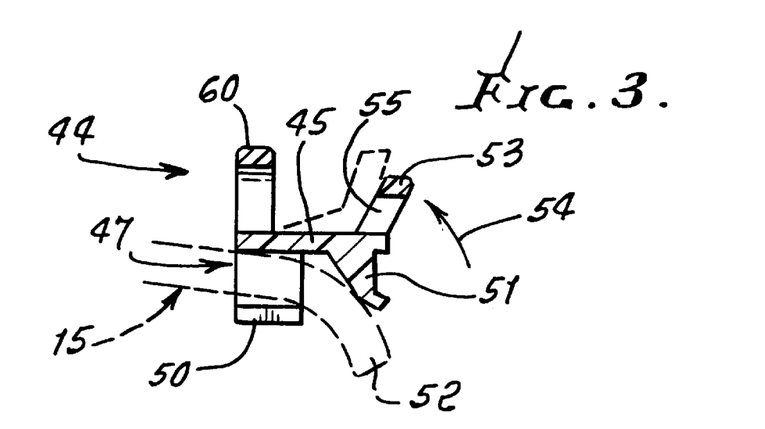
FIG. 3 is a section taken on lines 3—3 of FIG. 2.
Figure 4:
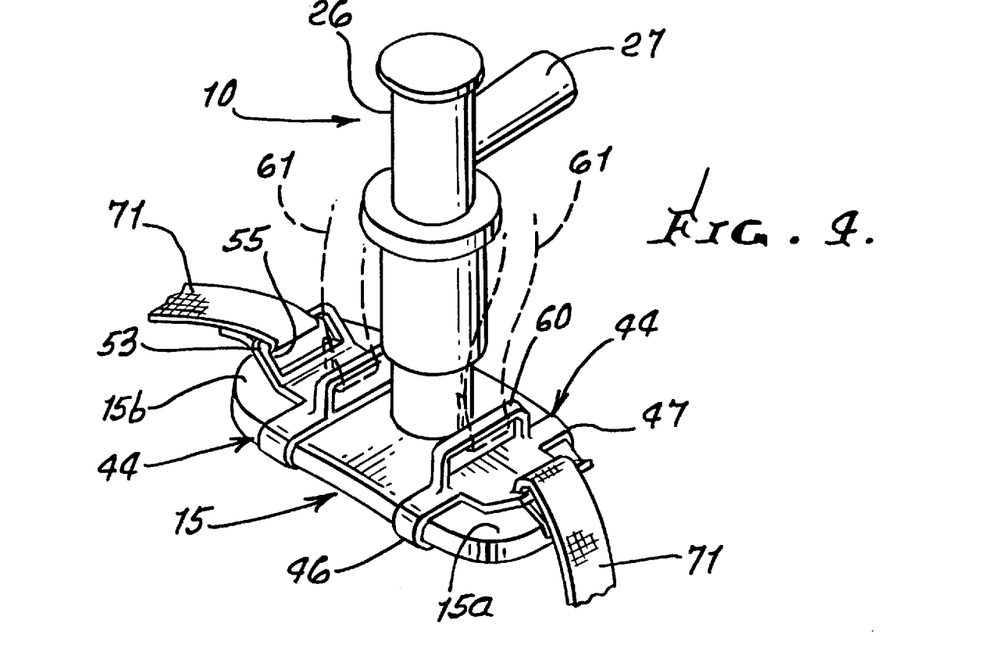
FIG. 4 is a perspective view showing clip attachment to a tracheostomy plate.
Figure 5:
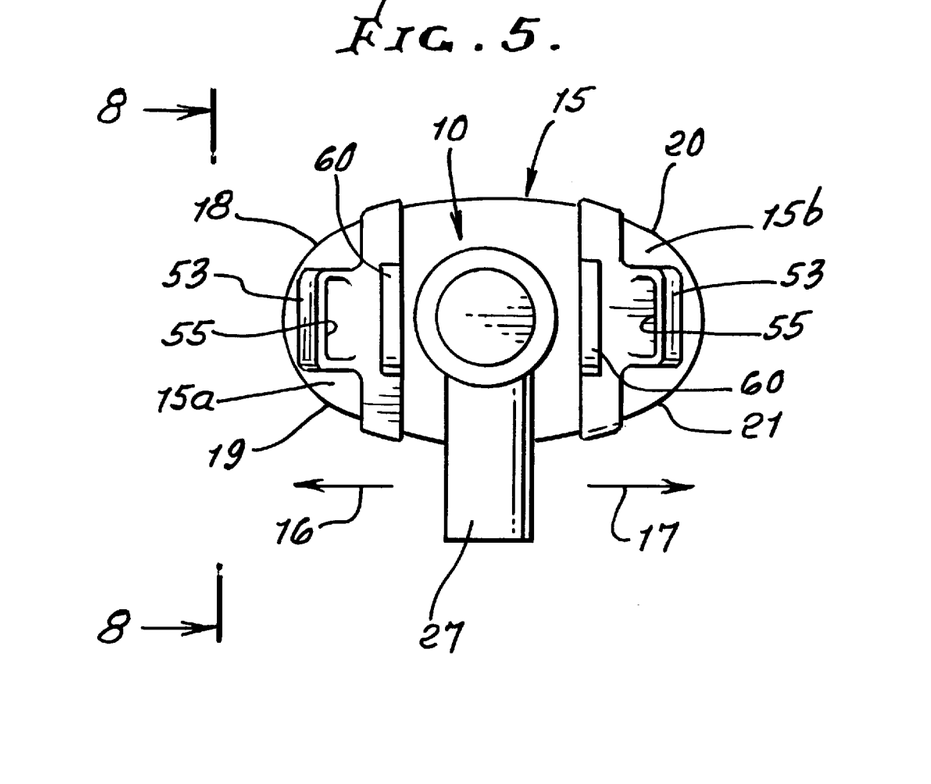
FIG. 5 is a top plan view showing two clips attached to the plate.
Figure 7:
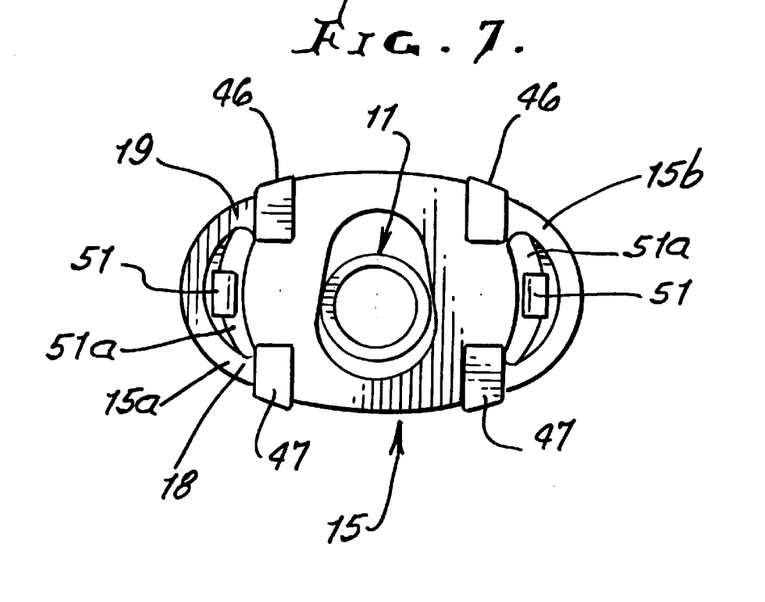
FIG. 7 is a bottom plan view showing legs of the two clips attached to the plate, and retention projections on the clips received in openings formed in the plate.

Referring to FIGS. 1–3, the plastic clip 44 includes a base section 45, and two legs 46 and 47. Each leg has an upper portion 48 integrally connected with the base section to slide along the top of the wing of plate 15, an outer portion 49, and a lower lip portion 50 slidable along the underside of the wing of plate 15. See also FIG. 7. Note that when the clip is fully laterally received on a plate wing, the leg outer portions 49 engage the wing edges 18 and 19, as seen in FIG. 7. At that time, a detent projection or post 51 is received downwardly into an opening 51a in the wing.

During slide reception of the clip on the wing, the outer, narrow, terminal portion 52 of the wing is resiliently bendable downwardly by the post, by sliding camming action, so that the post rides over terminal portion 52. When the post drops down into the opening, the legs come into close-fitting engagement with the wing edges 18 and 19, as shown in FIG. 7, providing a sturdy, safe and stable locking condition of the clip on the wing. Legs 46 and 47 engage the wing to hold the post in the opening.

In addition, the clip may be easily released from the wing as by pushing upwardly the upwardly angled rightwardly projecting section 53 of the clip (see arrow 54 in FIG. 3), to disengage the tang or post 51 from the opening 51a, followed by rightward slidable removal of the clip off the wing. Bending of base section 45 accommodates this section 53 upward movement.

Section 53 of the clip has the further function of providing an upward looping grip 55, for attachment of the band 71, as seen in FIG. 9. Attachment of the band to the wearer's neck serves to produce force in the arrow direction 56, which in turn has a component urging the grip 55 downwardly toward the plate, thereby retaining the post 51 in the retention opening 51a. Grip 55 therefore serves as a lever having multiple functions.

Also provided on each clip is a grip 60 that projects upwardly relative to base section 45 for retention of the tracheostomy tube retention band means 61, as best seen in FIG. 9. Grip 60 is located directly above the section 45 on which legs 46 and 47 and post 51 are carried, whereby upward force exerted by the band means 61 does not rock the clip to disengage post 51 from the opening.

Grips 55 and 60 are spaced above the level of clip base section 45, whereby attachment of the bands to the grips does not require dislodgment of the clip from the tracheostomy plate.

The method of the invention basically comprises:

a) providing clip means configured to embrace the wing, the band means attached to the clip means, b) displacing the clip laterally relative to the wing, to embrace the wing, c) and providing a detent connection on at least one of the clip and wing to releasably interconnect the clip and wing in response to the relative displacing of the clip to embrace the wing.

Figure 10:
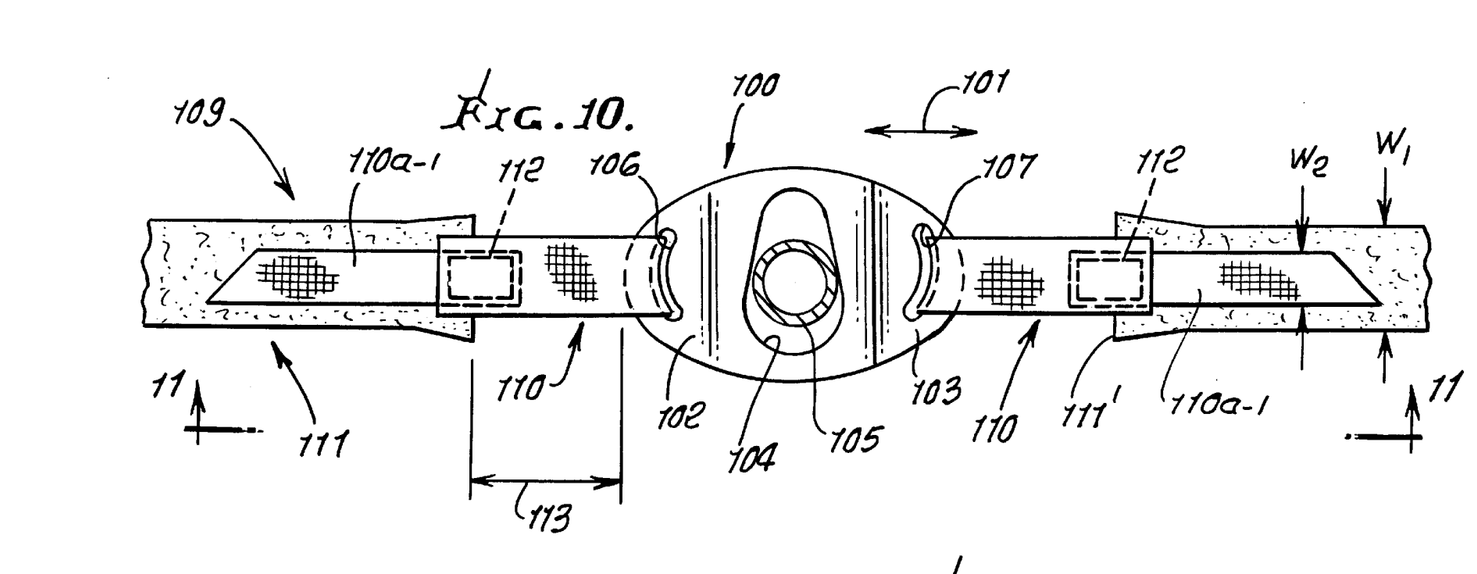
FIG. 10 is a plan view of modified connection apparatus.
Figure 11:
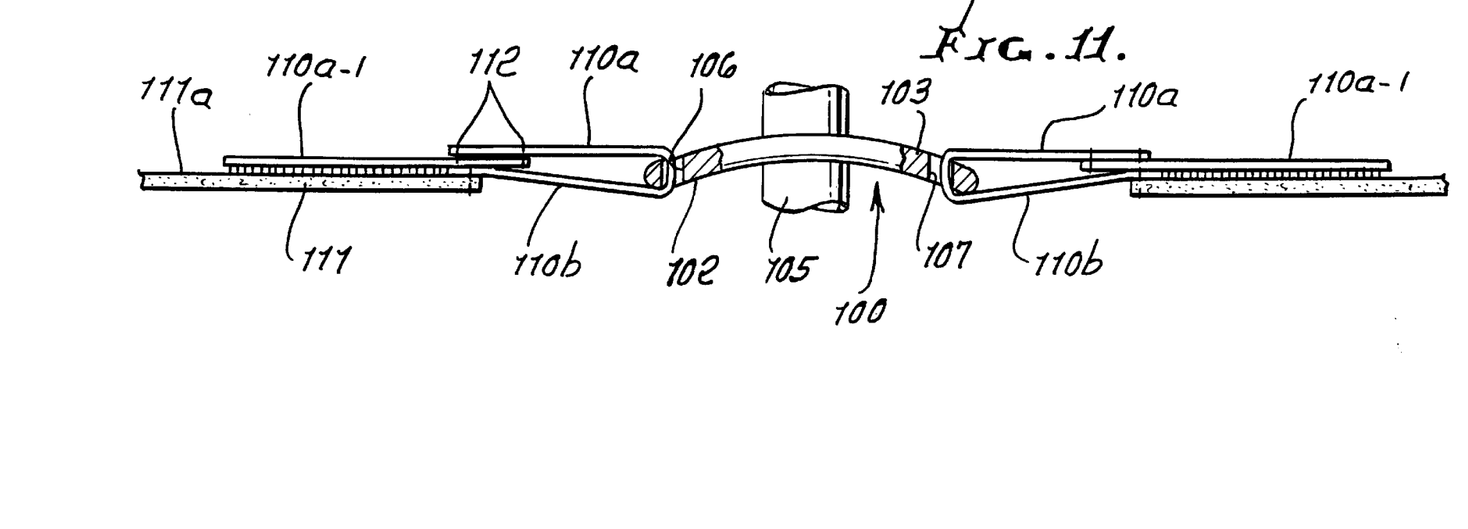
FIG. 11 is a view taken on lines 11—11 of FIG. 10.

Referring now to FIGS. 10 and 11, a tracheostomy neck plate 100 is longitudinally elongated in direction 101 and has a shallow curvature, as seen in FIG. 11. The plate includes two wings 102 and 103 at longitudinally opposite sides of a central through opening 104 that receives tracheostomy tubing structure 105 to be retained in position by the plate.

The two wings form first and second openings 106 and 107 that extend generally laterally, as shown. Those openings in the wings define first and second anchoring means. Plastic clips 44, as described above, are anchored to the plate 100, as at openings 106 and 107.

Flexible band means is provided, as at 109, to be connected to the clip-projecting sections 53, and an adjustable hook and pile connection, or connections, is or are provided for retaining the flexible band means adjustably connected to the clips. Such hook and pile connections may take the form of VELCRO connections.

In the preferred form shown, a first, thin, flexible band 110 of the band means loops over the section 53 and defines upper and lower sections 110a and 110b. The band section 10b is attached as by stitching to the upper side of the elongated padding 111 that fits about the wearer's neck, and at one end of 111. The band upper section 110a has a narrowed band 110a-1 attached to it by stitching, as at 112, the narrowed band extending lengthwise over the elongated padding 111.

Hook or pile structure on narrowed band 110a-1, and implementing pile or hook structure on the surface 111a of padding 111, adjustably interfit, as at 150, to allow lengthening or shortening of the gap 113 between wing 102 and the end of padding 111. This particular assembly allows very quick and easy adjustment of the narrowed band 110a-1, to facilitate adjustment of gap 113, to fit the overall band structure to the patient's neck. Similar structure is provided at the other end of the padding, to connect to section 53 of the second clip 44.

Note flaring end 111', and greater width $W_1$ of the padding than the width $W_2$ of the narrowed band 110a-1, which facilitate ease of adjustment lengthwise and widthwise of the band structure.

The bands 110 and 110a-1 of FIGS. 10 and 11 consist of thin, flexible fabric, which may be synthetic.

Figure 12:
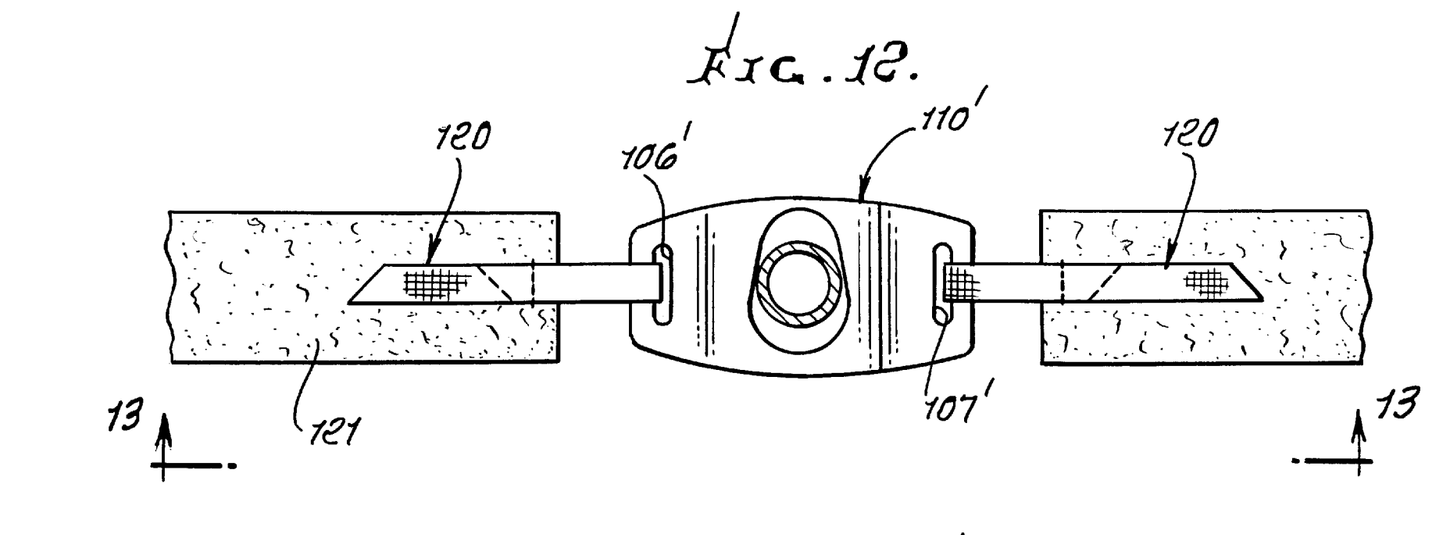
FIG. 12 is a plan view of a further modified connection.
Figure 13:
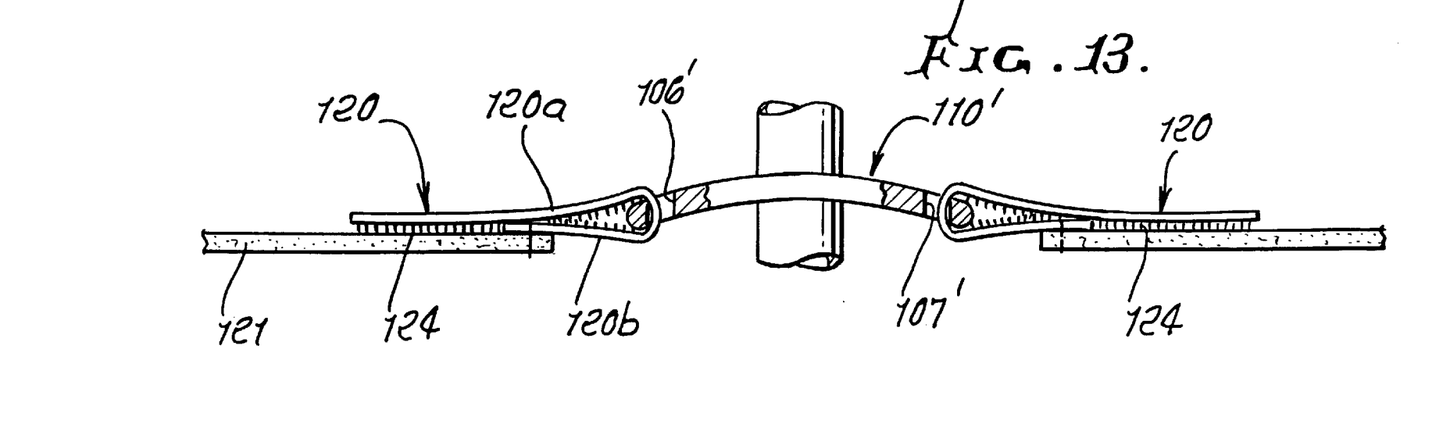
FIG. 13 is a view taken on lines 13—13 of FIG. 12.

FIGS. 12 and 13 show similar, but slightly modified, structure. A narrowed, flexible band 120 substitutes for the two bands 110 and 110a-1 of FIGS. 10 and 11; and the narrow band 120 loops over clip section 53. Lower extent 120b of band 120 is stitched to the much wider, elongated, flexible padding 121 that fits about the wearer's neck. Upper extent 120a of band 120 extends over the padding and has adjustable hook and pile (VELCRO) connection to it, as at 124. The same elements are provided at the other end of the padding, to connect to the second clip 44.

What is claimed is:

1. An apparatus for connecting flexible first band means to a tracheostomy neck plate having a first wing including a first opening therethrough, comprising:

a) first anchoring means including a clip on said first wing, the first band means connectible to the anchoring means, b) first adjustable hook and pile connections for retaining said first band means adjustably connected to the first anchoring means, c) and a first locking element carried by the clip to project through said first opening in response to assembly of the clip onto the wing, said opening having an edge, d) said first locking element being a projection having an angled surface for camming engagement with said tracheostomy neck plate at the edge of said opening, to deflect the tracheostomy neck plate in spaced relation to said hook and pile connection.

2. The apparatus of claim 1 wherein said band means includes a first ribbon.

3. The apparatus of claim 2 wherein said band means includes elongated padding, one of said hook and pile connections being on the first ribbon, and the other of the hook and pile connections being on the padding.

4. The apparatus of claim 3 wherein said padding has width greater than the width of the ribbon, the ribbon and padding adjustably interconnected at said hook and pile connections to selectively position the padding widthwise of the tracheostomy neck plate.

5. The apparatus of claim 1 wherein the tracheostomy neck plate has a second wing, and including second anchoring means including a second clip on said second wing, the band means also connectible to the second clip, and second adjustable hook and pile connections for retaining said band means adjustably connected to the second clip.

6. The apparatus of claim 5 wherein the tracheostomy neck plate second wing has a second opening therethrough, and said second anchoring means is configured to be anchored to said second opening through the tracheostomy neck plate and has a section above said opening, to pass said band means, there being a second locking element on the second clip, and the second clip anchored to the tracheostomy neck plate by reception of the second locking element into said second opening.

7. The apparatus of claim 6 wherein said band means includes first and second ribbons, said second ribbon fitted about said section.

8. The apparatus of claim 7 wherein said band means includes elongated padding having opposite end portions, said first and second ribbons attached to said padding opposite end portions, and projecting from said opposite end portions.

9. The apparatus of claim 8 wherein one of said hook and pile connections of the first anchoring means is located on the first ribbon, and the other of said hook and pile connections of the first anchoring means is located on one of the end portions of the elongated padding, and one of the hook and pile connections of the second anchoring means is located on the second ribbon, and the other of the hook and pile connections of the second anchoring means is located on the other end portion of the elongated padding.

10. The apparatus of claim 9 wherein said padding end portions have widths greater than the widths of said ribbons, and the ribbons are adjustably interconnected to the padding at said hook and pile connections to selectively position the padding widthwise, relative to the tracheostomy neck plate wings.

* * * * *